United States Patent [19]
Sheppard

[11] Patent Number: 6,019,005
[45] Date of Patent: Feb. 1, 2000

[54] AUTOMATIC SAMPLING APPARATUS FOR THE FARMER STOCK PEANUT PNEUMATIC SAMPLER

[75] Inventor: Harry T. Sheppard, Edison, Ga.

[73] Assignee: The United States of America as represented by the Secretary of Agriculture, Washington, D.C.

[21] Appl. No.: 08/915,687

[22] Filed: Aug. 21, 1997

[51] Int. Cl.[7] .............................. G01N 1/14; G01N 1/08
[52] U.S. Cl. ................................. 73/864.31; 73/863.01
[58] Field of Search ........................... 73/864.31, 863.01

[56] References Cited

U.S. PATENT DOCUMENTS

| | | | |
|---|---|---|---|
| 4,179,929 | 12/1979 | Redding | 73/864.31 |
| 4,616,515 | 10/1986 | Dencoine | 73/864.31 |

OTHER PUBLICATIONS

Sweeney, "Instrumentation and Automation" *Research Journal WPCF*, vol. 63(4), p. 424–425 (Jun. 1991).
Anthony et al.,"Experiences with Gin Process Control in the Midsouth and West" *Applied Engineering in Agriculture*, vol. 11(3), p. 409–414 (1995) month not given.
Davidson et al., "Comparison of Pneumatic and Automatic Spout Samplers to Determine Grade of Farmers Stock Peanuts" *Peanut Science*, vol. 18, p. 76–80 (1990–month not given).

Meagher et al., "Comparison of Pneumatic and Manual Probe Sampling of Kansas Farm–stored Grain Sorghum" *J. Econ. Entomol.*, vol. 79, p. 284–288 (Feb. 1986).
*Journal: ASHRAE transactions*, "Use of Programmable Controllers for HVAC Control and Facilities Monitoring Systems" 95(1), p. 492–497 (1989–month not given).

*Primary Examiner*—Thomas P. Noland
*Attorney, Agent, or Firm*—M. Howard Silverstein; John D. Fado; Gail E. Poulos

[57] ABSTRACT

A sampling apparatus for sampling agricultural commodities such as any legume, grain, vegetable, fruit, nut, etc., for grading and valuation purposes. The apparatus uses a programmable logic controller, sensors, and logic software to operates a sampling and collection system The sampling apparatus includes a sampling tube which obtains the required samples from a trailer-like vehicle to a sample bin and then to a collection chute. In this manner, the sampling apparatus automatically obtains a representative sample of the agricultural commodity contained within the trailer and allows for accurate grading and valuation.

12 Claims, 26 Drawing Sheets

Microfiche Appendix Included
(4 Microfiche, 358 Pages)

AUTOMATIC SAMPLING APPARATUS FOR THE FARMER STOCK PEANUT PNEUMATIC SAMPLER

MICROFICHE APPENDIX

A Microfiche Appendix containing 4 microfiche containing 358 frames is included.

BACKGROUND OF THE INVENTION

Field of the Invention

Individual lots of agricultural commodities defined herein to mean any legume, grain, vegetable, fruit, nut, etc. which capable of being sampled are required to be graded and valued for marketing purposes. The method used in sampling and evaluating these commodities has remained unchanged for over 30 years. Currently, untrained laborers operate sampling equipment, which includes a pneumatic sampler, to obtain samples of the commodity in question. Frequently, the sampling practices are faulty, due to various factors such as untrained laborers and faulty sampling practices used on the manually operated samplers. This results in samples which are often not representative of the batch being graded and valued.

To obtain a sample for the pneumatic sampler, operators handle manual controls to maneuver a motorized carriage to a plurality of positions, as determined by the batch size, above the batch of peanuts obtained in a trailer-like vehicle. The sampler operates on tracks about 20 feet above ground, which exposes operators to unfavorable work conditions, heat, cold and dust. As a result, operators often reduce the frequency of the maneuvering and sampling procedure, which leads to inaccurate sample readings and thereby results in incorrect grading valuation of the batch of the commodity being sampled. Additionally much of the sampling procedure is non-uniform, which further leads to erroneous evaluation of the commodity. There is a need to provide an improved sampling apparatus which overcomes the problems encountered by the manually operated sampling practice.

SUMMARY OF THE INVENTION

It is, therefore, an objective of this invention to provide a system which automates sampling and evaluating procedures thus overcoming the obstacles of manual sampling given above.

It is another objective of this invention to provide a system which determines the position and size of a trailer carrying the commodity and to accurately sample the batch.

It is yet another objective of this invention to provide an agricultural sampling system which obtains a sample for each batch of the commodity being graded and valued.

It is yet another objective of this invention to provide an agricultural sampling system for automatically obtaining a plurality of samples from a given batch.

It is yet another objective of this invention to provide an agricultural sampling system which automatically determines sample size and delivers the sample to a ground level sample holding bag.

It is yet another objective of this invention to provide an agricultural sampling system which automatically returns the unused portions of the samples to the trailer-like vehicle.

It is yet another objective of this invention to provide an agricultural sampling system having various sensors for automatically determining positions of the trailer-like vehicle, a sampling apparatus, and a sample holding bag.

These and other objectives are realized by the automated sampling apparatus of the present invention. The present invention overcomes the problems encountered in currently used manual operation and sampling practices by providing an automatic operation of a pneumatic sampler. A programmable logic controller, sensors, and logic software all operate the sampling apparatus to obtain the required sample for proper grading and valuation.

DETAILED DESCRIPTION OF THE INVENTION

The automatic sampling apparatus is a system which determines the position and size of a trailer like vehicle or trailer T carrying an agricultural commodity and accurately samples the commodity. The expression "agricultural commodity" as defined hereinabove, includes any legume, grain, vegetable, fruit, nut, etc. which is capable of being sampled.

Figure 1:
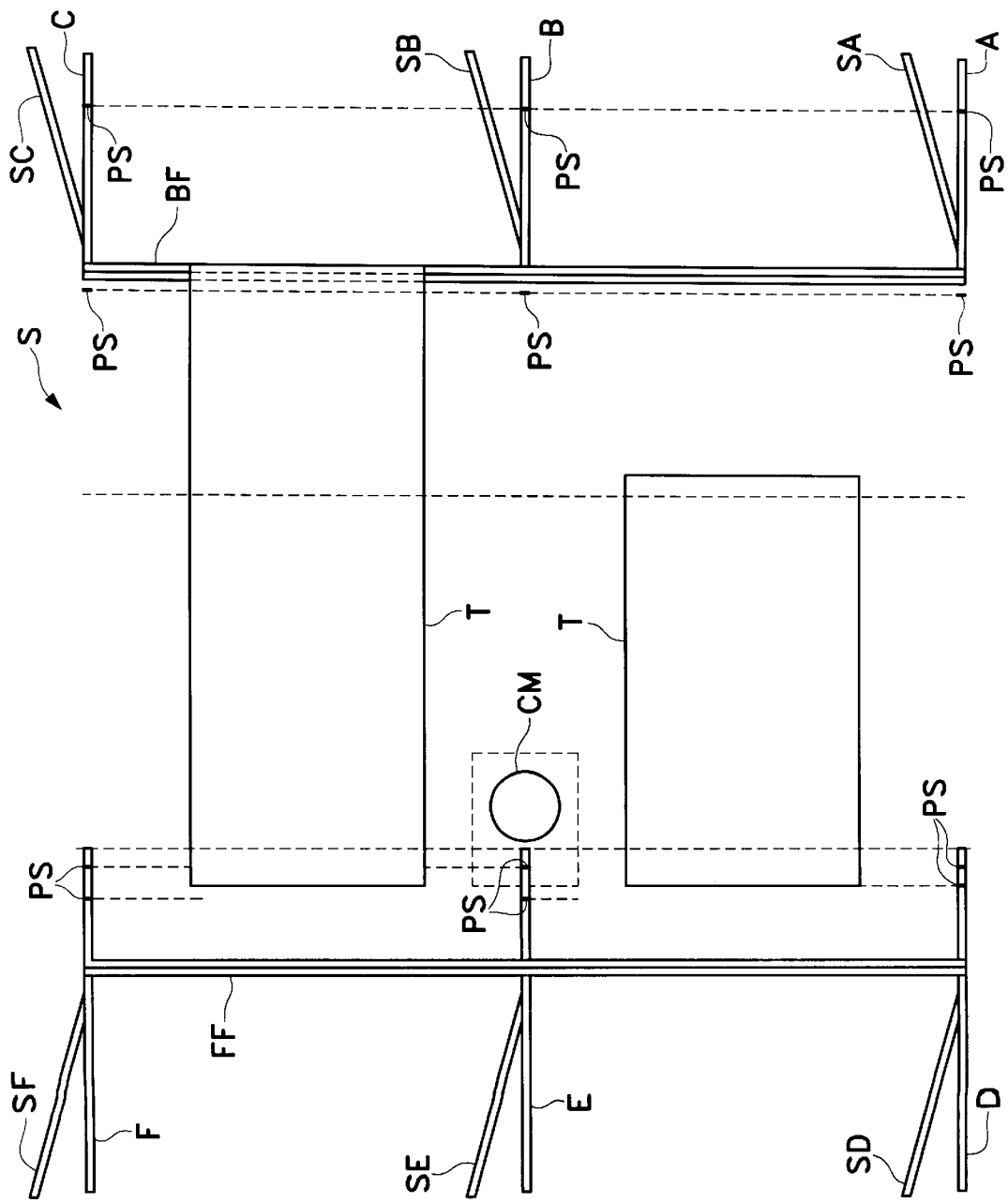
FIG. 1 shows the sampling apparatus frame.

As shown in FIG. 1, the sampling apparatus S has a metal frame F having a back BF and a front FF frame portion. Frame portion BF includes legs A, B and C; each having a corresponding support leg sA, sB and sC. Frame portion FF includes legs D, E and F; each having a corresponding support leg sD, sE and sF.

As shown in FIGS. 1,4, 5, 8 and 10–23, attached to or associated with frame portions BF and FF is a system of sensors (identified as "ps" in FIGS. 1 and 26) which enable the proper positioning and sampling of trailers T containing harvested commodities. The holding areas for the trailers T during positioning and sampling are known as bays. These sensors include a front of trailer limit photo switch 20 and a front of trailer in range photo switch 21 which are both diffuse reflex switches; a front of trailer slow down warning photo switch 23, an about 28 feet or longer trailer photo switch 30, an about 21 feet to about 27 feet trailer photo switch 27 and an about 14 feet to about 20 feet trailer photo switch 24, all of which are thru beam sensors. Sensors 20, 21, 22 and 23 are located on three mounting brackets 19 affixed to legs D, E and F approximately six feet and four and one-half inches from the base of the tires of vehicle T. Mounting brackets 19 can be anything suitable for mounting sensors such as for example angle iron support brackets. The mounting brackets are made up of a support bracket, a mounting back plate and a support brace. The support bracket is about 45 ¼" in length and is a piece of about 3"×3"×¼" angle iron attached to the base of a about 15 ¼" long mounting back plate. An approximately 1 ½"×¼" flat support brace is affixed at one end to the mounting plate and at the other end to the support bracket at about a 45° angle. Brackets 19 are mounted at one end perpendicular to the inside facing surface of legs D, E and F. Sensor 20 is located approximately 2 feet in from the leg end of bracket 19 on legs D–F. Sensor 21 is located approximately 3 feet 1-¼ inches form the leg end of bracket 19 on leg F. Sensor 22 is also located approximately 3 feet 9-¼ inches from the leg end of bracket 19 on legs D–F. Sensor 24 is positioned approximately 15 feet 9-¼ inches from the inside of legs D–F on trailer sensor pole 29 at approximately 6 feet 4-½ inches from the base of the tires of vehicle T. Pole 29 can be anything suitable for supporting a sensor at the desired height. Sensor 30 is positioned approximately 28 feet 9-¼ inches from the inside of legs D–F directly in line with sensors 24 and 27. Sensor 27 is located on support legs sA, sB and sC and is mounted on a bracket 28 at the end opposite to where bracket 28 is affixed to the support leg. Cables (not shown) extending from each sensor are attached to a power source (not shown) and to a programmable logic controller PLC as will be discussed hereinbelow.

Figure 2:
FIG. 2 shows the components of sampling cage.

As shown in FIG. 2, a motorized sampling means SM includes a sampling platform SP which travels over tracks BR and BL, in the x-direction, a sampling cage SF which travels along tracks BL and BR, in the y-direction, and a sampling tube ST which travels in the z- direction. The x-direction, y-direction and z-direction are as defined in the upper right hand corner of FIG. 2. The movement of sampling means SM in the x, y and z directions allows it to travel to a bay area where a trailer T is positioned. Once the sampling means is properly positioned over a trailer T to be sampled, the sampling tube ST collects the sample with the aide of pressure hose PH suction hose SH and collection fan (not shown). The suction hose SH provides a pneumatic fluid to the sampling tube ST for removing samples from the trailer T, whereas the pressure hose PH supplies an adjustable fluid force, preferably air, to aid in suction and displacement of sample. The sample tube ST may remove five or more samples from a trailer T, depending upon analysis requirements determined by the PLC. Once a sample or a plurality of samples are removed, they are temporarily held in sample bin SB. The sample is then divided down through housing DB. In a preferred embodiment of this invention, various sensors guide the sampling means to its correct position as will be described hereinbelow. The sampling platform SP may also be manually controlled using the manual control panel MCP as is currently done in the manual samplers.

Figure 17:
FIG. 17 shows location of electric brake.
Figure 18:
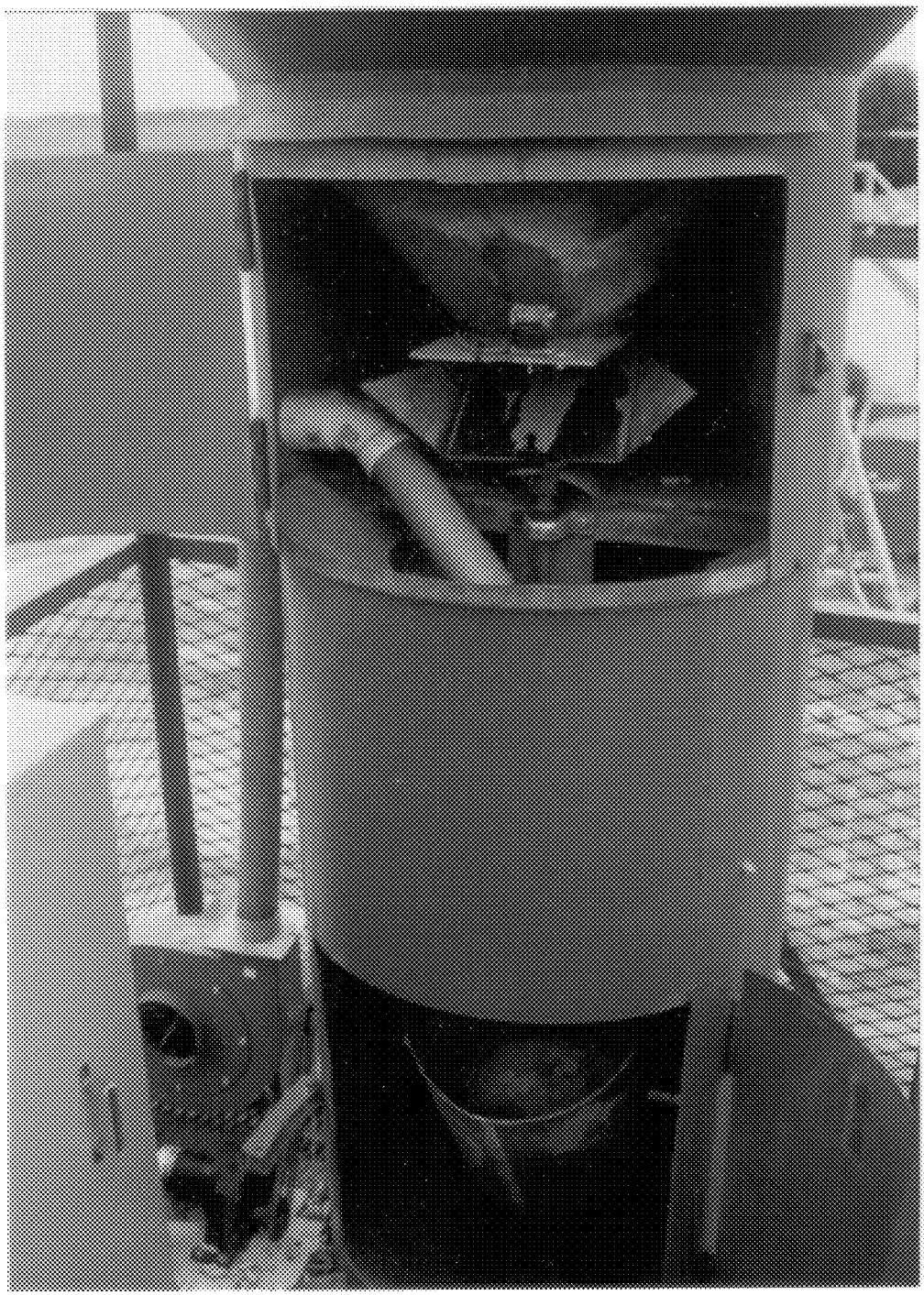
FIG. 18 shows components of sample bin.
Figure 19:
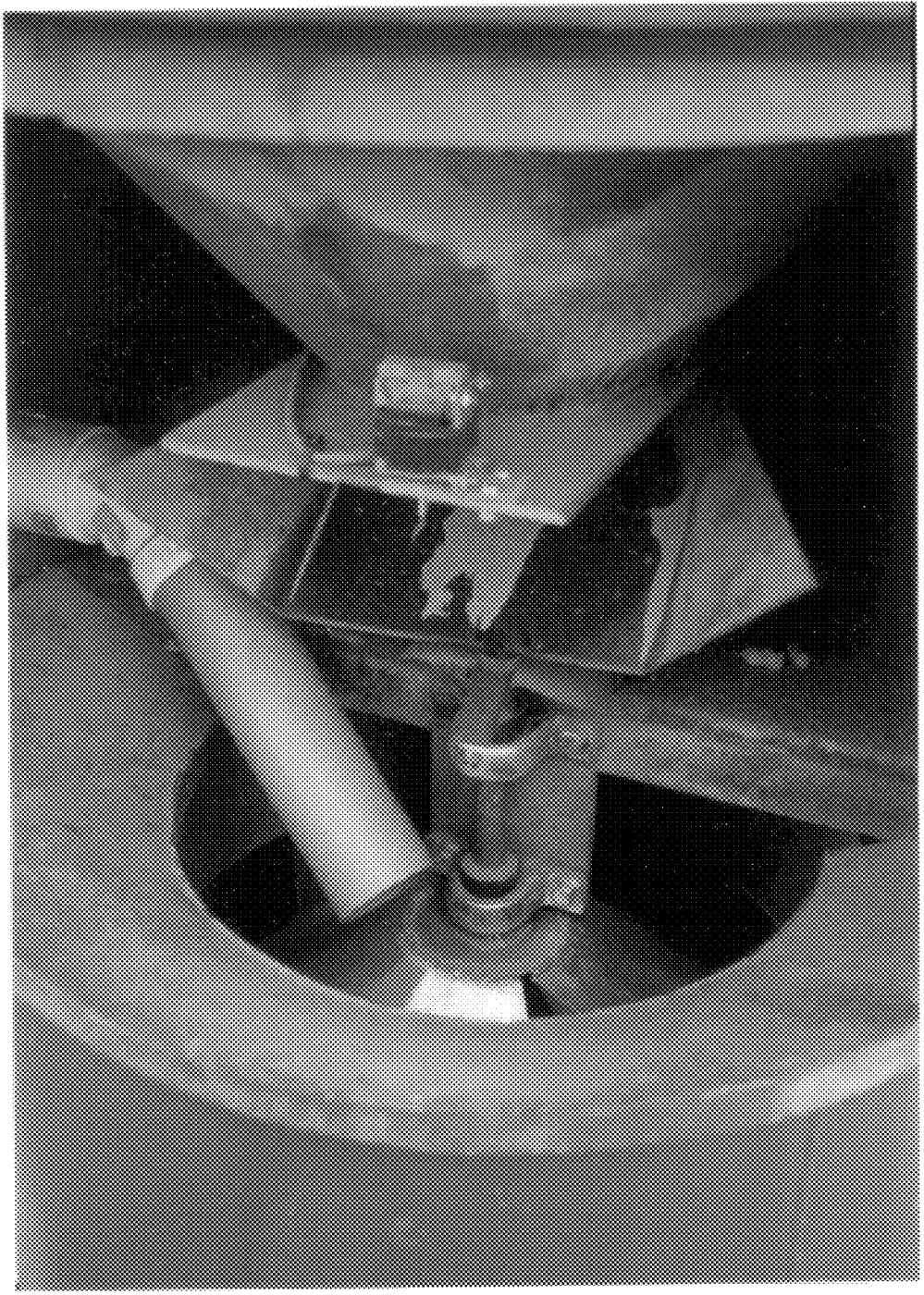
FIG. 19 shows sample divider.

After obtaining the sample, the sampling means SM positions itself over the center of trailer T. Solenoid 50 is activated as shown in FIG. 18, dumping the sample into the divider 57, which extracts a portion of the sample, preferably ⅛ th of the total sample, and deposits the portion into the sample bucket 52. The remaining sample falls back into the trailer T via the sample sock 58(FIG. 17). After returning the remaining or excess sample, the divider 57 is cleaned out by the blower 54, which pushes air through tube 55 and then through piping 56 as shown in FIGS. 18 and 19.

Figure 3:
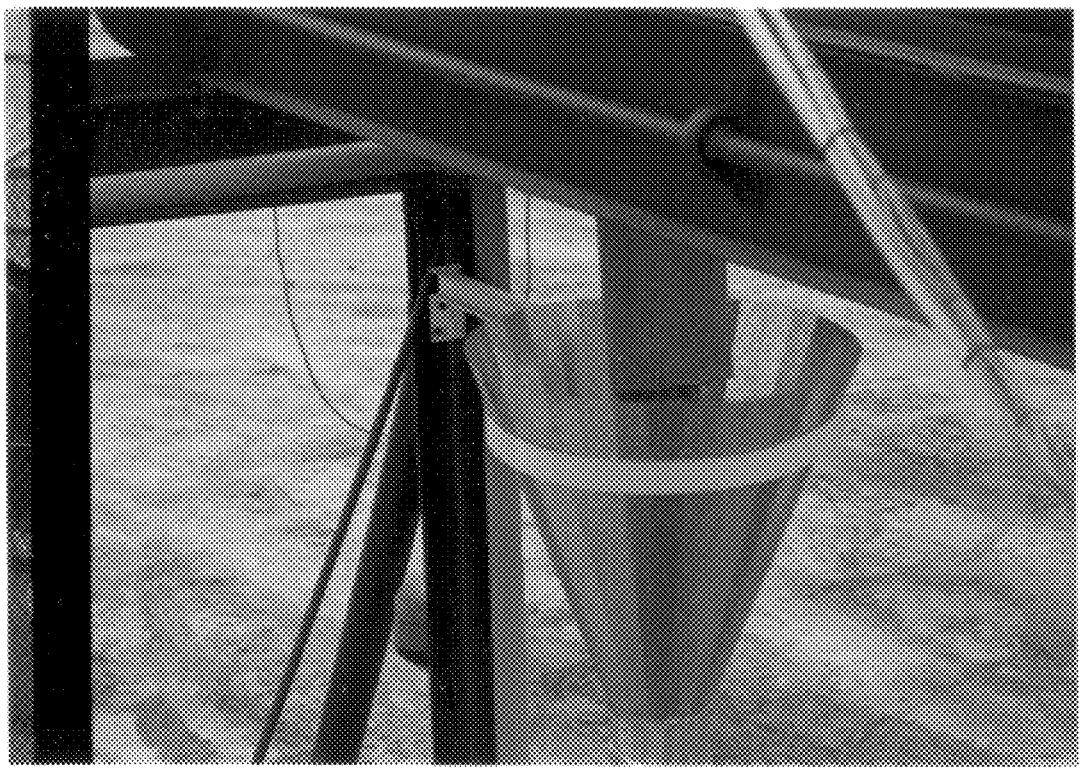
FIG. 3 shows the upper portion of the sampling chute.
Figure 4:
FIG. 4 shows the sampling chute.
Figure 5:
FIG. 5 shows sample bag support bracket.

The obtained sample is dumped into a collection means CM as identified in FIG. 1. The actual position of the collection means CM as shown in FIG. 1 may be anywhere within the boundaries as set forth by the front and back frame FF and BF, dependent upon optimal positioning. As shown in FIG. 3, the collection means include a sample funnel support ring 1, a sample collection funnel 2, sample bag full indication light 8, and sample sock 58. FIG. 4 shows the proximity of the collection means with respect to tracks BL and BR, and the positioning sensors. As shown in FIG. 4 the collection means also includes a sample slide tube 3, and sample bag support ring 4. FIG. 5 shows the sample bag sensor support bracket chain 5, sample bag in place sensor 6, and sample bag full sensor 7. The sample bag sensors may be any suitable sensors known in the art. Of interest are diffuse reflect photoelectric and capacitive proximity sensors. The sensors are capable of emitting an audible alarm, light indicators or both. The sensors work in conjunction with the positioning sensors as shown in FIG. 1 and will be explained below.

Figure 6:
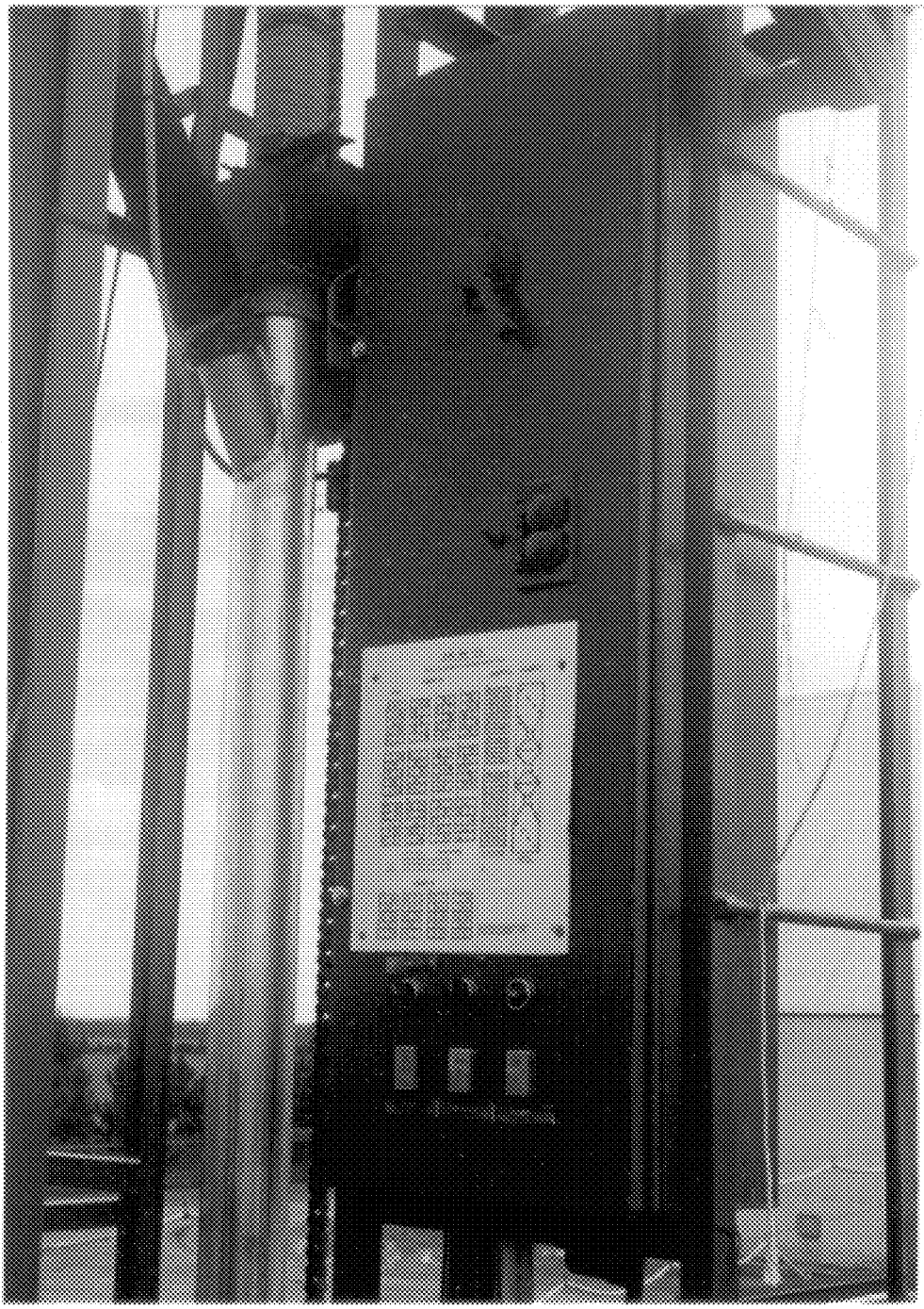
FIG. 6 shows components of manual to automatic switching.
Figure 7:
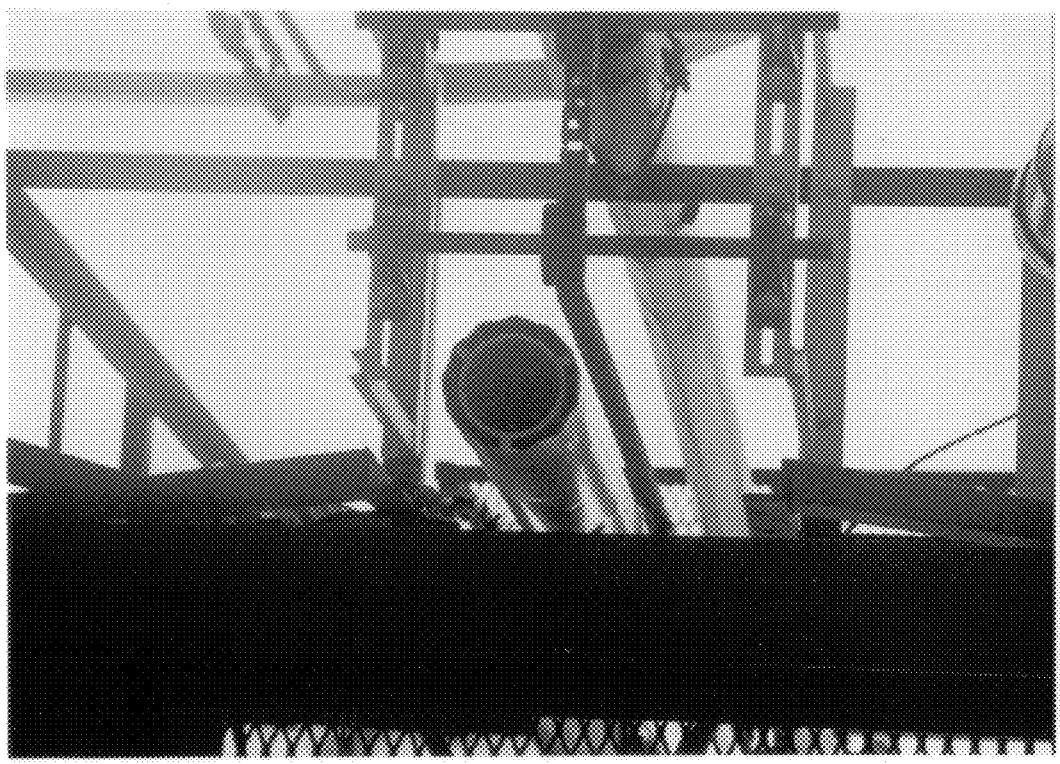
FIG. 7 shows the components of the chain support.
Figure 8:
FIG. 8 shows the positioning sensors.
Figure 9:
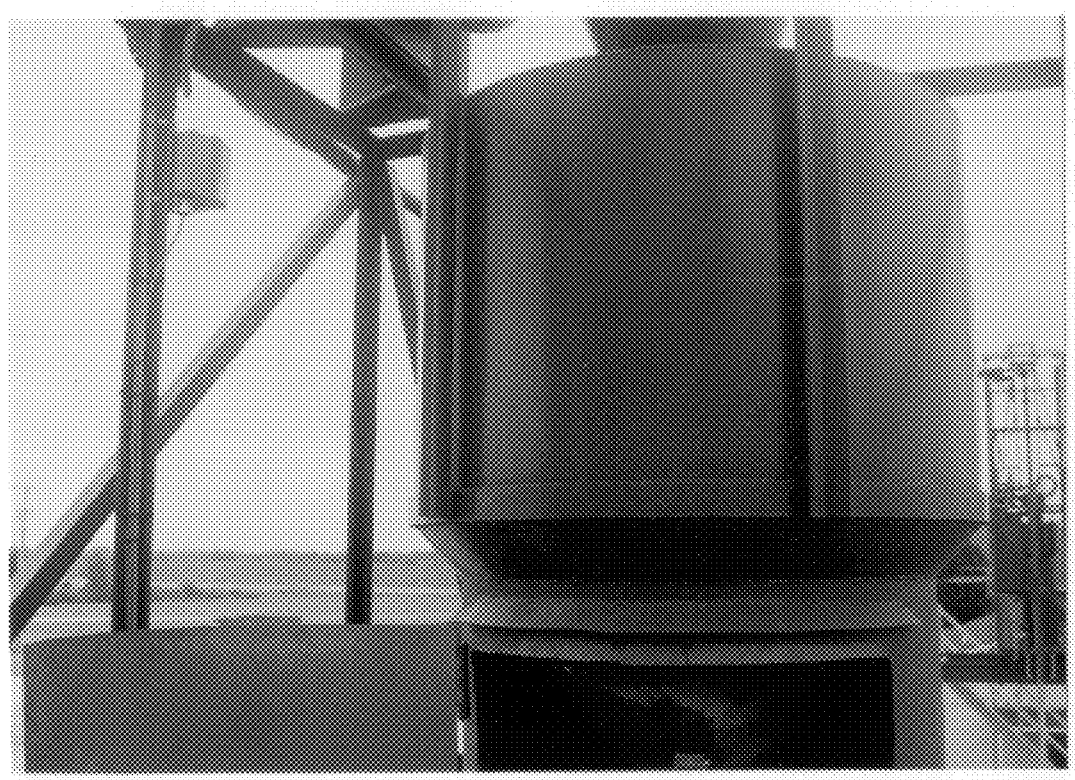
FIG. 9 shows warning horn.

As shown in FIGS. 2 and 6 the manual control panel (MCP) on sampling cage SF allows the sampling apparatus to be operated manually. The MCP has an automatic to manual switch 9, a manual electric brake release cord 10, and a tube raising and lowering chain 11. The supports shown in FIG. 7 include chain support brackets 15 and 16, chain idlers 12 and 13, and chain sprockets 14. FIG. 8 shows sampling in process. A warning light 17 is activated when the sampling means SM is in operation. An audible alarm 62, as shown in FIG. 9, warns an operator that the trailer is in place, and warns personnel that the sampling apparatus S is about to be operated.

Figure 10:
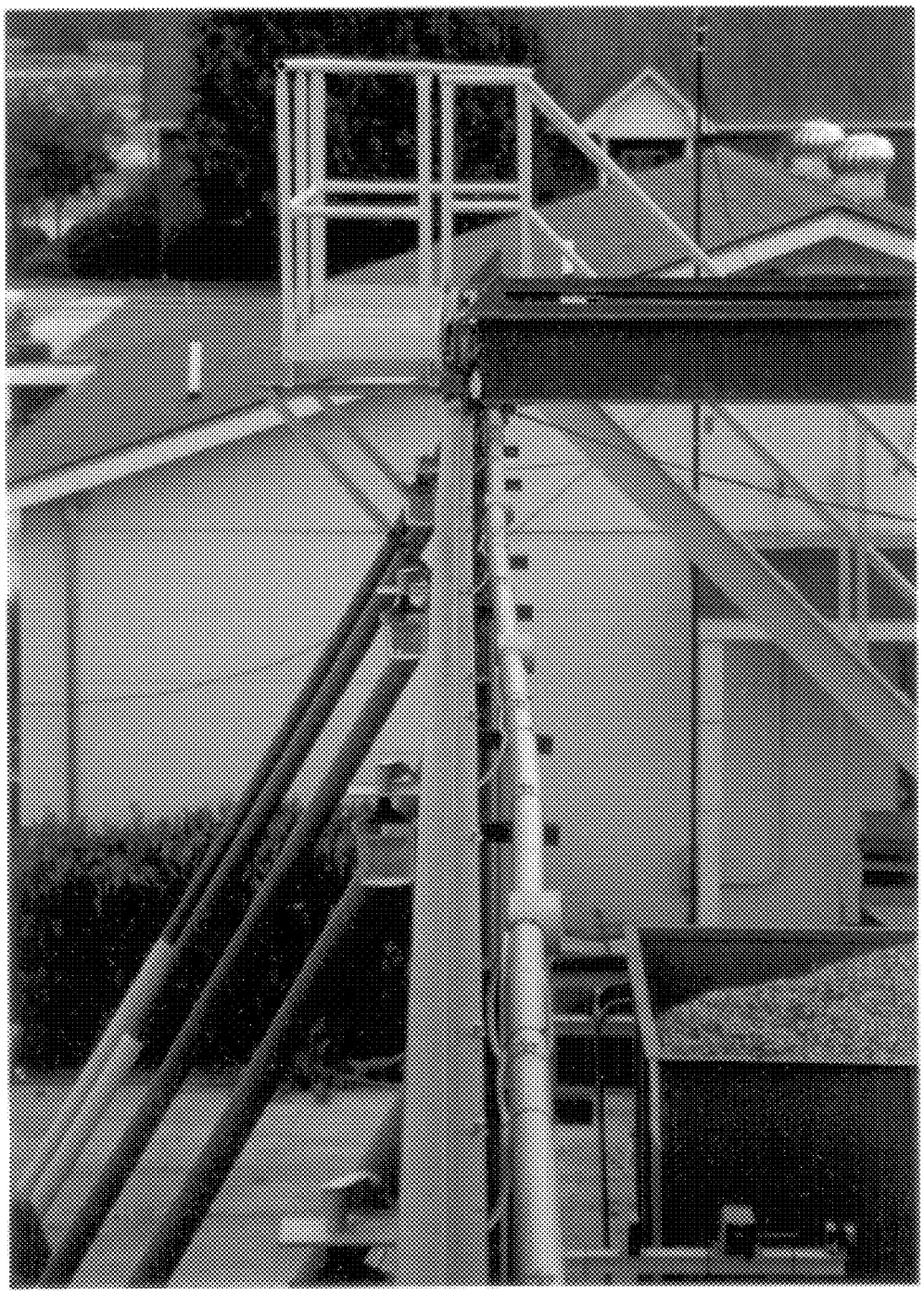
FIG. 10 shows bay positioning bolts and lights.
Figure 11:
FIG. 11 shows dumping positioning components.
Figure 12:
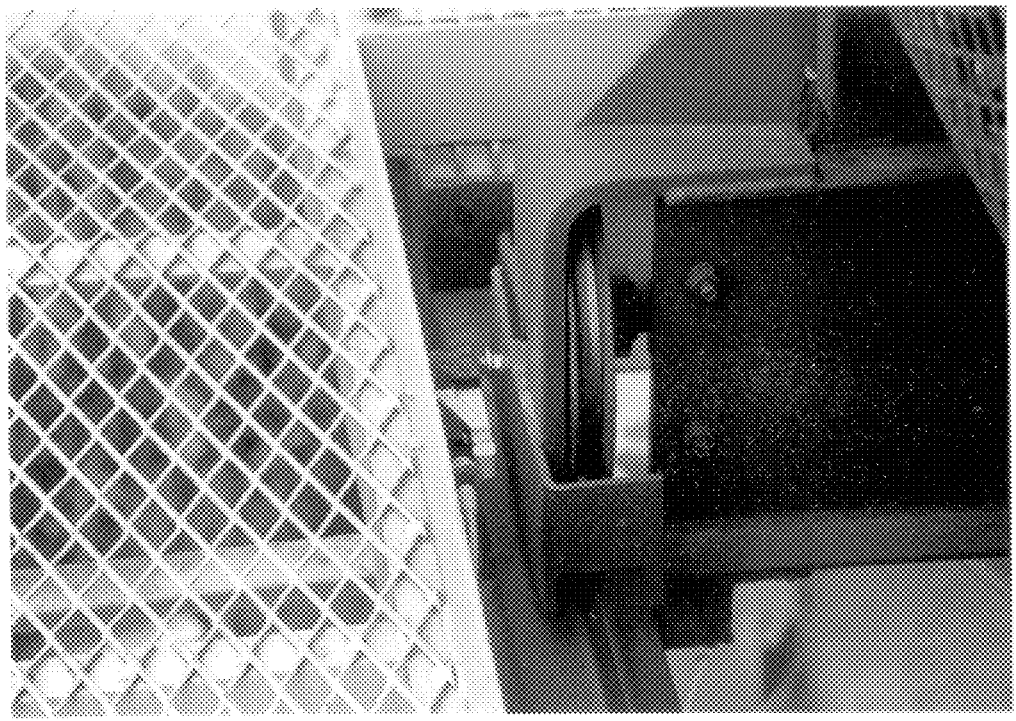
FIG. 12 shows home sensors.
Figure 13:
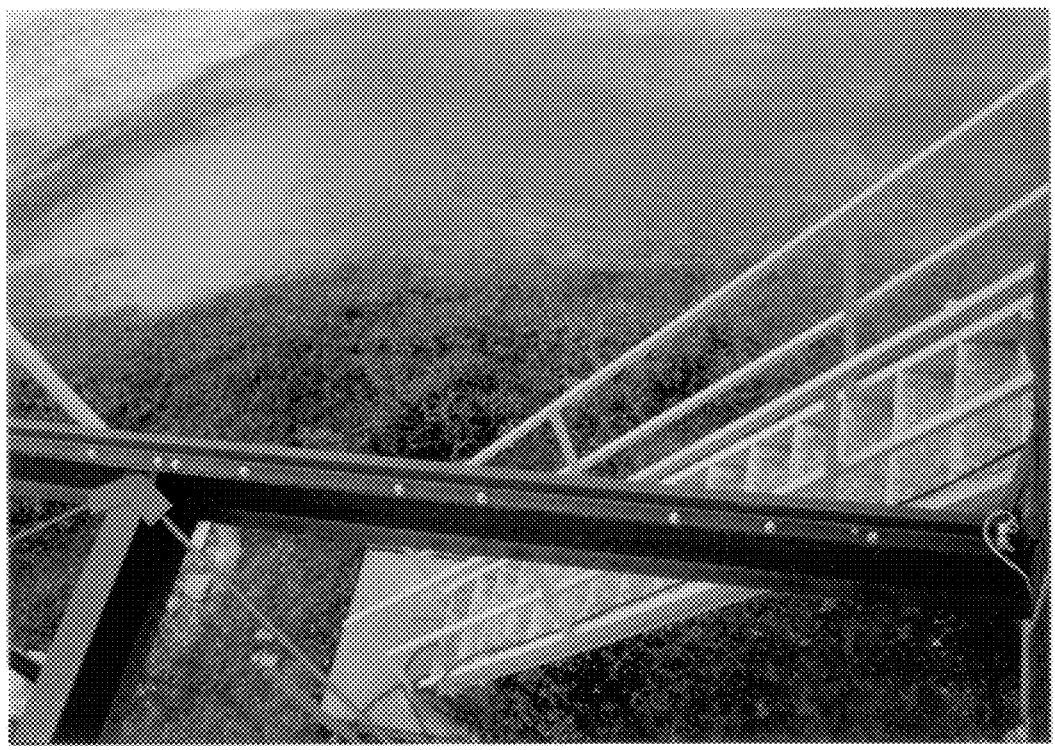
FIG. 13 shows sample cage positioning bolt.
Figure 14:
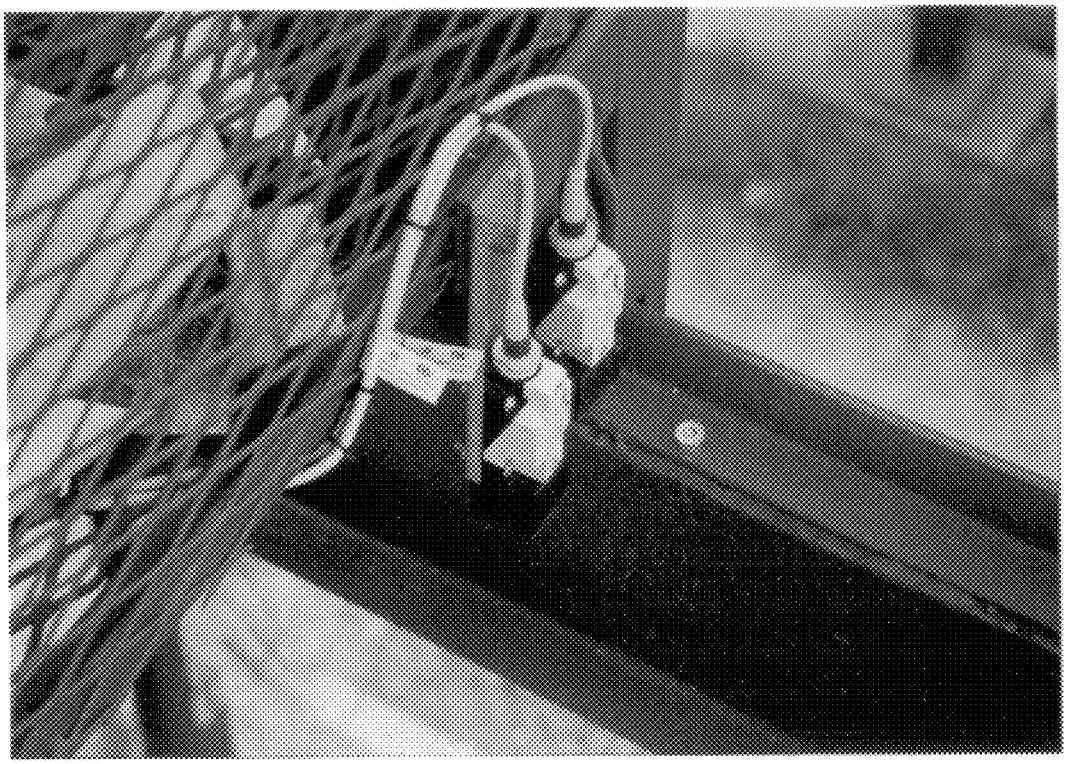
FIG. 14 shows sample cage sensors.

Once a sample is obtained, the sampling platform moves in the x-direction under the guidance of position bolts 31 and sensor 32(FIG. 10). The X direction movement for the sampling pattern and bay selection is accomplished by position bolts 31 and sensor 32. Bay warnings 33 emit a signal (optical or audible) to alert the operator to the positioning of the sample platform, as shown in FIG. 10. The BR stop position for dumping is done by sensor 36 which is mounted on track BR and sensing bolt 37, both shown in FIG. 11. BR at stairway/home position is sensed by sensor 38 and sensing bolt 39 which are shown in FIG. 12. The sample cage SF then moves in the y- direction for the sampling pattern and sample dumping through positioning bolts 34 and sensor 35 shown in FIG. 13, and sensors 43 and 45 and positioning bolts 44 which are shown in FIG. 14.

Figure 15:
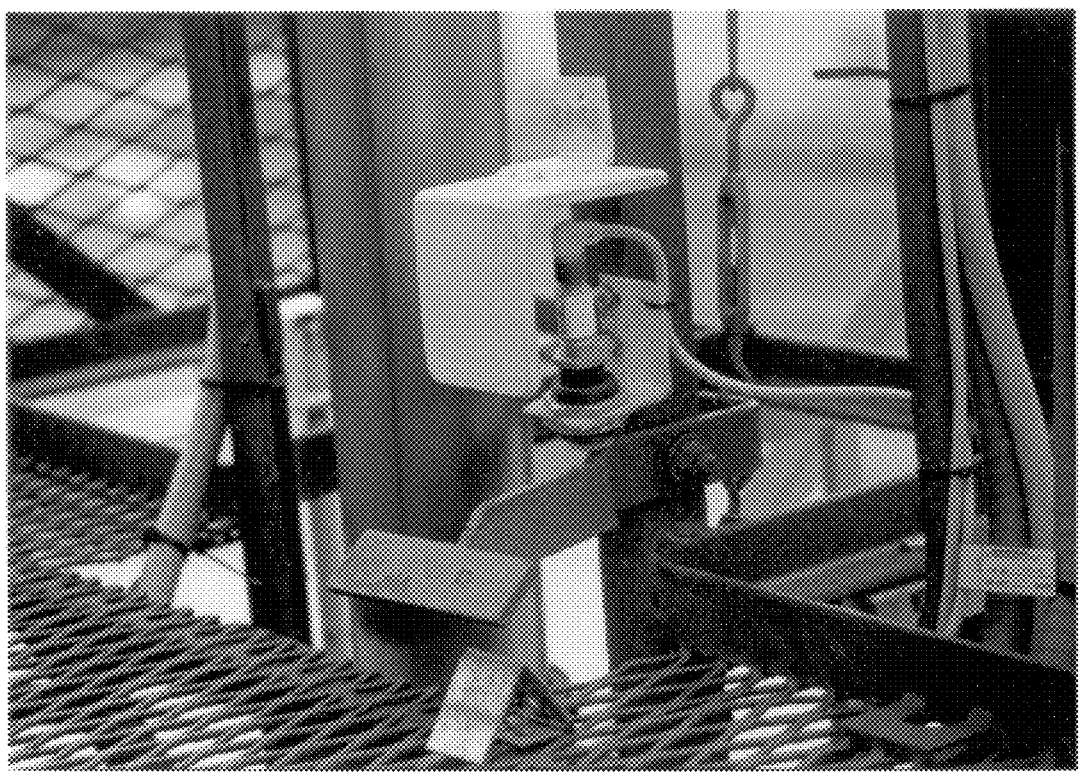
FIG. 15 shows brake pedal components.
Figure 16:
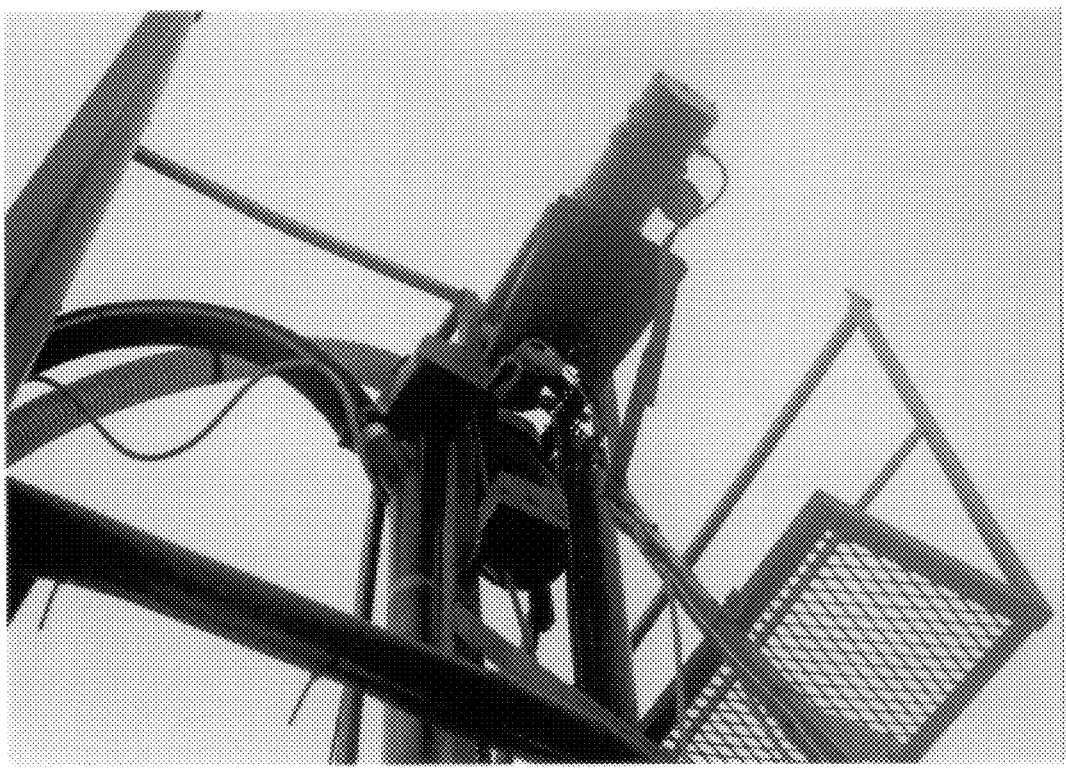
FIG. 16 shows electric brake.

As shown in FIG. 15, to allow for manual override, the sampling means includes a manual brake pedal, which is held in the disengaged position by bracket 60 during the automatic operation of the sampling system. A sensor 40 is used to detect the position of the manual brake pedal. Bracket 41 is used to support the sensor 40 and bracket 42 is used to protect sensor 40. As shown in FIGS. 16 and 17, an electric brake 68 signaled by sensor 67 stops the sampling tube ST movement.

Figure 20:
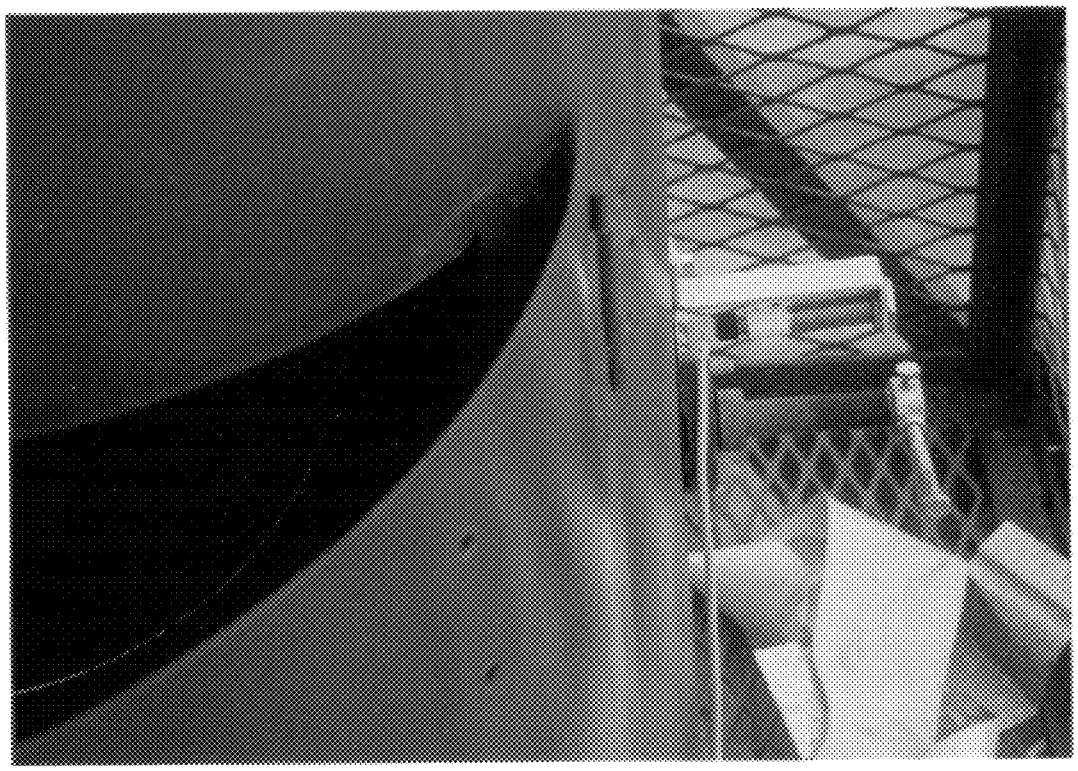
FIG. 20 shows sample bucket rotation sensor.

Once obtained, the sample is stored in sample bin SB. The sample is then passed through a sample door 51 operated by a solenoid gate 50 to the divider 57 which separates a portion of the obtained sample for analysis purposes, as discussed above(FIG. 18). The divider 57(FIG. 19) delivers the portion of the sample to the motorized bucket 52(FIG. 18) positioned on a shaft 49 and rotated by a motor 53(FIG. 20), stores the portion of the sample and delivers the portion into collection funnel 2(FIG. 3). A sensor 46, held by sensing bracket 47 properly positions the bucket 52 for proper dispensing into funnel 2, as shown in FIGS. 18 and 20. The portion of the sample then passes through sample slide tube 3 to sample bag holder 4 and then into a collection or sample bag(FIG. 4). The sample bag sensor 7 through light 8 indicates when the bag is full(FIGS. 3, 4 and 5). The bag is then removed for analysis. The remaining sample is dumped back into the trailer T via the sample sock 58(FIG. 3).

Figure 21:
FIG. 21 shows door sensor.
Figure 22:
FIG. 22 shows stop go light.
Figure 23:
FIG. 23 shows stop go light position.
Figure 24:
FIG. 24 shows enclosures.

Additional features of the sampling means includes a open/close cage door sensor 61, as shown in FIG. 21. FIGS. 22 and 23 show the driver stop and go lights and the sensor mounting bracket 19. Remote program logic controller PLC enclosure 64 and twenty-four volt direct current power supply is housed in enclosure 65 which is shown in figure 24.

Figure 25:
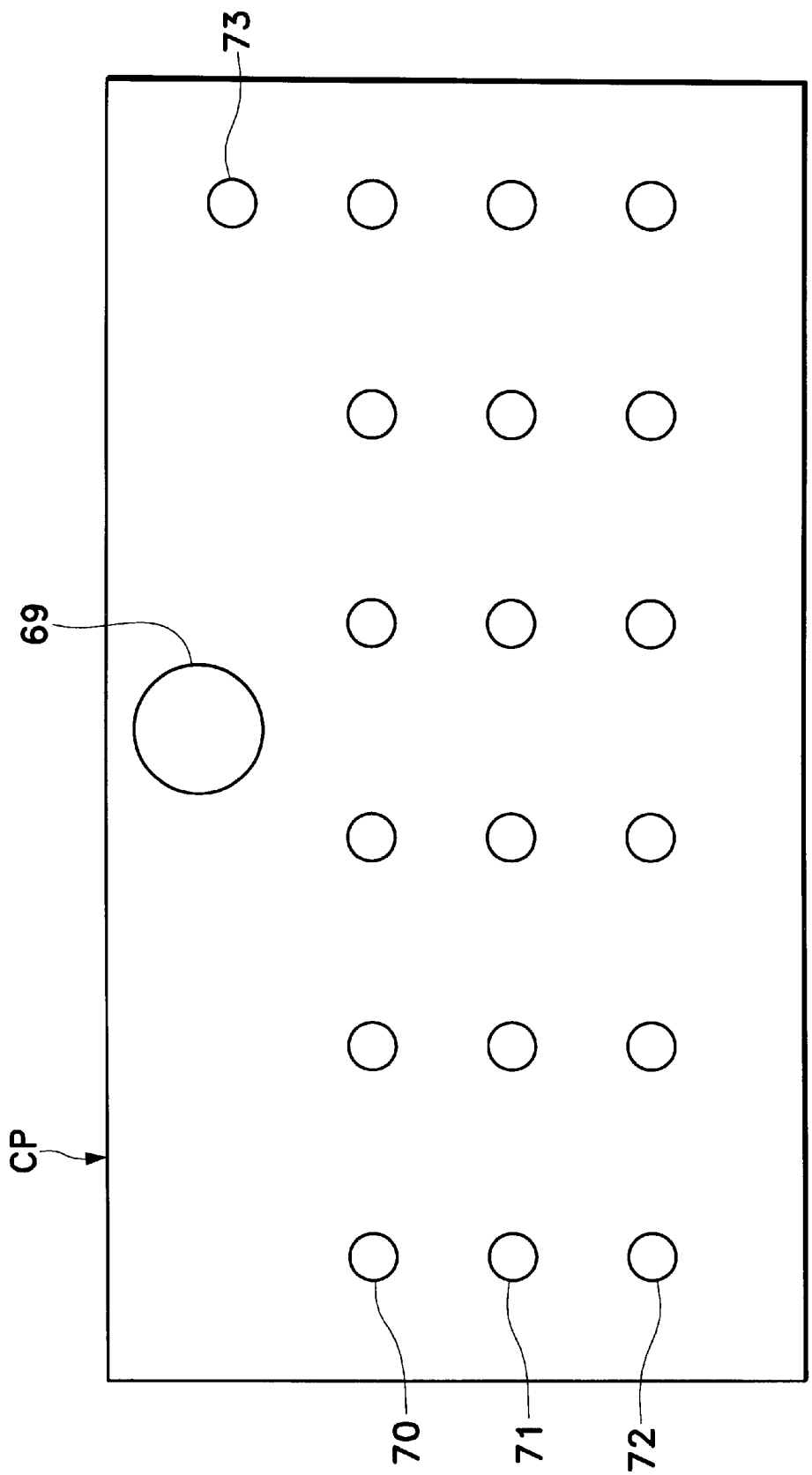
FIG. 25 shows the master control panel.

The control panel CP as shown in FIG. 25, is located inside a grading room positioned outside of the sampling apparatus S area is be used to automatically operate the sampling apparatus S. The control panel CP including a kill switch 69 will manually override all PLC functions and stop the sampling means SM, a load size selection switch 70 allows the operator to manually choose load sizes, a visual trailer selection push button switch 71 and an on/off manual to automatic switch 72 which connects the MCP to the PLC.

Figure 26:
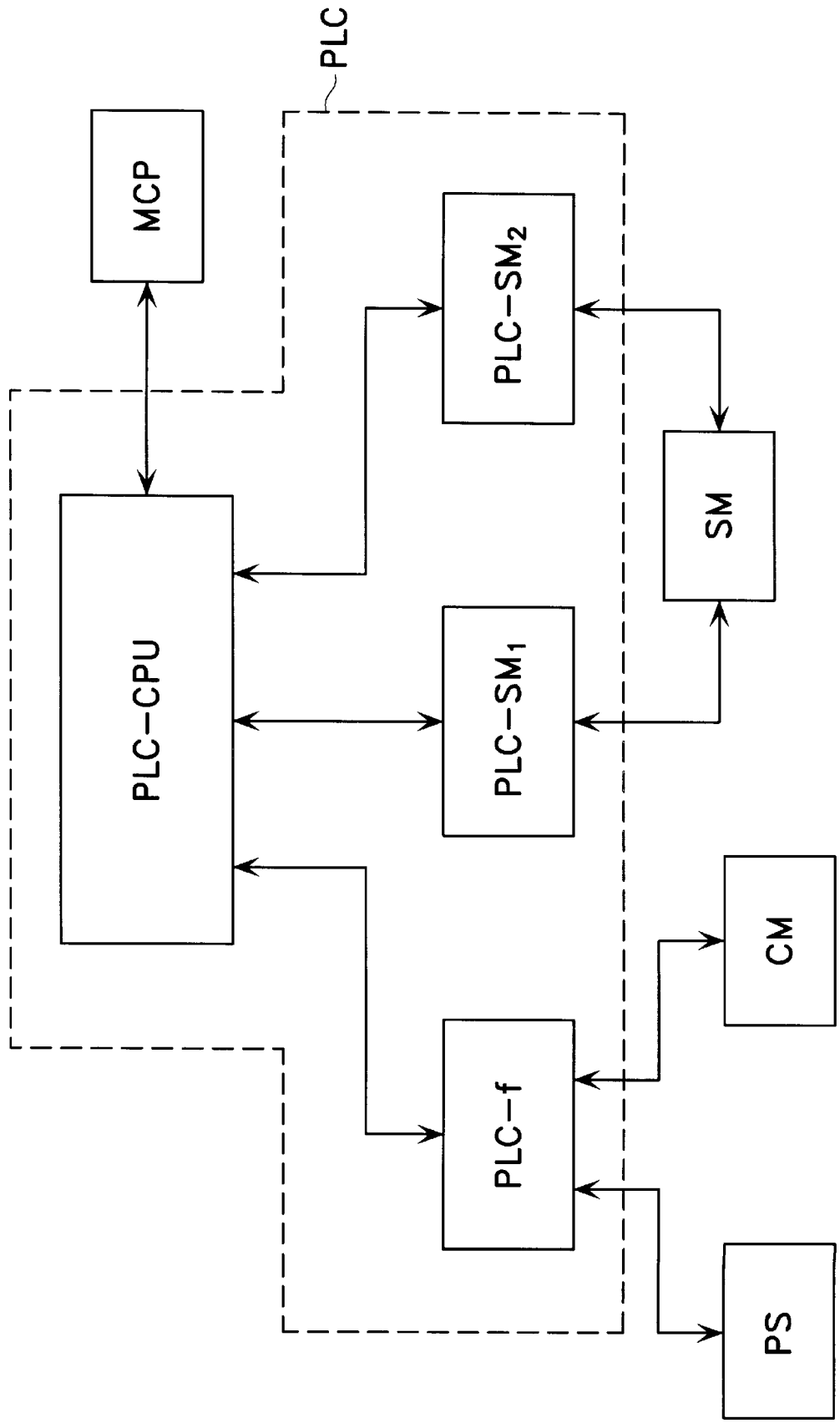
FIG. 26 shows the flow of the PLC's

In the preferred embodiment all functions of the sampling apparatus S are controlled by the PLC. As shown in FIG. 26, the PLC includes a main central processing unit PLC-CPU. As shown in FIG. 26, the PLC-CPU is connected to the control panel CP to operate the apparatus S automatically. The PLC-CPU is also connected to a remote PLC for the frame, PLC-f, and two remote PLCs for the sampling means, PLC-SM, and PLC-SM$_2$. When in automatic control, the PLC-CPU sends and receives signals from the position sensors ps indicating trailer T position, trailer size and load size, via the remote PLC-f. The PLC-CPU utilizes the information through a derived logic software to then send and receive appropriate signals to and from the sampling means sensors via the remotes PLC-SM$_1$ and PLC-SM$_2$. The sampling means SM may obtain five or more samples from each trailer T depending upon the agricultural commodity and the type of analysis required, as will be readily understood by one of ordinary skill in the art. The PLC-CPU directs the sampling means SM to return excess sample to trailer T via the PLC-SM$_1$ and PLC-SM$_2$. The PLC-CPU then utilizes the collection means CM to bag the sample as discussed hereinabove. The sampling apparatus, in this manner, allows automatic sampling to be facilitated, thereby overcoming the manual sampling procedures endured in the past.

The foregoing detailed description is for the purpose of illustration. Such detail is solely for that purpose and those skilled in the art can make variations therein without departing from the spirit and scope of the invention.

We claim:

1. A sampling apparatus for sampling an agricultural commodity comprising: a frame having a front frame and a back frame portion, wherein said front frame comprises a plurality of legs with each of said legs having a corresponding support leg;

said back frame comprising a plurality of legs, with each of said legs having a corresponding support leg, wherein said front and back frame portions so as to define at least one bay area;

a sampling means constructed so as to attain at least one sample from a trailer positioned in said bay area;

a plurality of positioning sensors positioned on said legs on said front frame portion, and at least one sensor positioned on said back frame portion, said positioning sensors constructed so as to determine whether the vehicle is properly positioned within said bay area;

a collection means constructed so as to collect said sample from said sampling means; and a programmable logic controller having a derived logic software, said programmable logic controller constructed so as to automatically control said sampling apparatus.

2. A sampling apparatus for sampling an agricultural commodity as recited in claim 1 and further comprising:

said sampling means comprising a sampling platform, a first and second track, a sampling cage, and a sampling tube, said sampling means constructed so as to move along said first and second tracks, said sampling means further comprising a plurality of sampling sensors positioned on said platform, said first and second track, said sampling cage and said sampling tube, said plurality of sampling sensors constructed so as to obtain said sample from said vehicle.

3. A sampling apparatus for sampling an agricultural commodity as recited in claim 2 and further comprising:

at least one sampling platform sensor, said at least one sensor constructed so as to move said platform in an x-direction on said first and second track;

at least one sampling cage sensor, said at least one sensor constructed so as to move said cage in a y-direction on said first and second track;

at least one sample tube sensor constructed so as to move said tube in a z-direction;

said sensors constructed so as to position said sampling means over said trailer so as to obtain said sample from said trailer; and said sample tube further comprising a pressure hose, and a suction hose, constructed so as to provide a pneumatic sectioning system to said tube.

4. A sampling apparatus for sampling an agricultural commodity as recited in claim 3 and further comprising:

said collection means comprising a sample collection funnel, a sample funnel support ring and a sample slide tube;

said sample collection funnel connected to and in flow communication with said sample slide tube, said collection funnel constructed so as to be supported by said support ring;

said sample slide tube constructed so as to be removably attached to a collection bag;

said bag further constructed so as to be supported by a sample ag support ring;

a first and second collection sensor, said first sensor positioned on said collection means and constructed so as to determine proper bag placement of said bag, said second sensor positioned on said collection apparatus and constructed so as to determine whether said bag holds said sample.

5. A sampling apparatus for sampling an agricultural commodity as recited in claim 4 and further comprising:

said positioning sensors, said sampling means sensors, and said collection means sensors selected from a group consisting of diffuse reflect photoelectric and capacitative proximity sensors.

6. A sampling apparatus for sampling an agricultural commodity as recited in claim 5 and further comprising:

said programmable logic controller constructed so as to automatically control said device, said controller comprising a main central processing unit and connected to a remote programmable logic controller for said frame and two remote programmable logic controllers for said sampling means, said main central processing unit constructed so as to send and receive signals from said sensors through said remote programmable logic controller for said frame and said two remote programmable logic controllers for said sampling means.

7. A sampling apparatus for sampling an agricultural commodity as recited in claim 6 and further comprising:

a control panel constructed so as to automatically operate said sampling apparatus, said control panel comprising a kill switch constructed so as to override said programmable logic controller and stop said sampling means, a load size selection switch, constructed so as to allow an operator to manually choose load sizes of said trailer, a visual trailer selection push button switch and a manual to automatic switch, said manual to automatic switch constructed so as to connect said manual control panel with said programmable logic controller.

8. A sampling apparatus for sampling an agricultural commodity comprising: a frame having a front frame and a back frame portion, wherein said front frame comprises a plurality of legs with each of said legs having a corresponding support leg;

said back frame comprising a plurality of legs, with each of said legs having a corresponding support leg, wherein said front and back frame portions so as to define at least one bay area;

a sampling means constructed so as to attain at least one sample from a trailer positioned in said bay area;

a plurality of positioning sensors positioned on said legs on said front frame portion, and at least one sensor positioned on said back frame portion, said positioning sensors constructed so as to determine whether the vehicle is properly positioned within said bay area;

a collection means constructed so as to collect said sample from said sampling means;

a programmable logic controller having a derived logic software, said programmable logic controller constructed so as to automatically control said sampling apparatus; and a control panel constructed so as to automatically operate said sampling apparatus, said control panel comprising a kill switch constructed so as to override said programmable logic controller and stop said sampling means, a load size selection switch, constructed so as to allow an operator to manually choose load sizes of said trailer, a visual trailer selection push button switch and a manual to automatic, said manual to automatic switch constructed so as to connect said manual control panel with said programmable logic controller.

9. A sampling apparatus for sampling an agricultural commodity as recited in claim 8 and further comprising:

said sampling means further comprising a sample divider constructed so as to separate a portion of said obtained sample, said divider constructed so as to deliver the portion of the sample to a motorized bucket positioned on a shaft and rotated by a motor, said bucket constructed so as to store the portion of the sample and deliver said portion into said collection funnel via said slide tube into said bag;

said bucket further comprising a sensor held by a sensing bracket, said sensor constructed so as to properly position the bucket for properly dispensing said portion of said sample into said funnel.

10. A sampling apparatus for sampling an agricultural commodity as recited in claim 9 and further comprising:

said collection means comprising a sample collection funnel, a sample funnel support ring and a sample slide tube;

said sample collection funnel connected to and in flow communication with said sample slide tube, said collection funnel constructed so as to be supported by said support ring;

said sample slide tube constructed so as to be removably attached to a collection bag;

said bag further constructed so as to be supported by a sample ag support ring;

a first and second collection sensor, said first sensor positioned on said collection means and constructed so as to determine proper bag placement of said bag, said second sensor positioned on said collection apparatus and constructed so as to determine whether said bag holds said sample.

11. A sampling apparatus for sampling an agricultural commodity as recited in claim 10 and further comprising:

said programmable logic controller constructed so as to automatically control said device, said controller comprising a main central processing unit and connected to a remote programmable logic controller for said frame and two remote programmable logic controllers for said sampling means, said main computer processing unit constructed so as to send and receive signals from said sensors through said remote programmable logic controller for said frame and said two remote programmable logic controllers for said sampling means.

12. A sampling apparatus for sampling an agricultural commodity as recited in claim 11 and further comprising:

said positioning sensors, said sampling means sensors, and said collection means sensors selected from a group consisting of diffuse reflect photoelectric and capacitative proximity sensors.

\* \* \* \* \*